United States Patent [19]

Elsohly et al.

[11] 4,315,862
[45] Feb. 16, 1982

[54] PROCESS FOR PREPARING CANNABICHROMENE

[75] Inventors: Mahmoud A. Elsohly; Carlton E. Turner, both of Oxford, Miss.

[73] Assignee: The University of Mississippi, University, Miss.

[21] Appl. No.: 44,350

[22] Filed: May 31, 1979

[51] Int. Cl.$^3$ .................................. C07D 311/58
[52] U.S. Cl. ............................ 260/345.2; 424/283
[58] Field of Search .................................... 260/345.2

[56] References Cited

PUBLICATIONS

Kane et al., JACS, 90, 6551 (1968).
Crombie et al., J. Chem. Soc. (C), 796 (1971).
Crombie et al., J. Chem. Res. S (Synopses), 1977, (5), 114–115, (C.A. 87:102470s).

*Primary Examiner*—Nicky Chan
*Attorney, Agent, or Firm*—William D. Stokes

[57] ABSTRACT

The preparation of cannabichromene (CBC) and homologues thereof by condensation of citral with a substituted resorcinol in the presence of a primary amine, and the use of these compounds to induce hypothermia and reduce inflammation in mammals, is disclosed. Preferably, the cannabichromene is administered as a novel composition, in combination with a pharmaceutically acceptable diluent carrier. A new compound 2-methyl-2(4-methyl-pent-3-enyl)-5-hydroxy-7-methylchromene (CBC-C$_1$).

10 Claims, No Drawings

PROCESS FOR PREPARING CANNABICHROMENE

BACKGROUND OF THE INVENTION

There has been for many years an ongoing search for the discovery and development of more effective antiinflammatory and hypothermia inducing agents which can be administered to mammals in therapeutically effective dosages with minimal side effects. There is also an economic need for such agents which are relatively simple to produce from readily available non-costly reagents. A wide variety of compounds have demonstrated antiinflammatory properties, as for example pyrazolidinediones, arylalkanoic acids, carboxylic acid amides, and salicylates. Anthranilic acid and certain of its derivatives, such as mefenamic acid, flufenamic acid, and N-benzoyl-anthranilic acid, have also exhibited antiinflammatory activity as described, for example in the article by M. W. Whitehouse, "Biochemical Properties of Anti-Inflammatory Drugs," *Biochem. Pharmacol.*, 16, pp. 753–760 (1967). Aspirin, of course, is probably the most commonly used antiinflammatory and antipyretic agent. Most of the known antipyretics have the disadvantage of often dangerous side effects such as causing circulatory collapse.

The compound 2-methyl-2(4-methyl-pent-3-enyl)-5-hydroxy-7-pentylchromene or cannabichromene (CBC) is well-known in the prior art, occurring naturally as a cannabinoid constituent of *Cannabis sativa L*. The reported usefulness of cannabichromene is primarily that of intermediate in the synthesis of related compounds, such as cannabicyclol.

The known synthesis of cannabichromene have not been entirely satisfactory, owing to historical poor yields and problems associated with purification of the product.

Exemplary of such prior art synthesis routes are the cyclodehydrogenation of cannabigerol with chloranil in benzene or with 2,3-dichloro-5,6-dicyanobenzene (DDQ). Perhaps a more important route for the synthesis of cannabichromene and related compounds has been the condensation of citral with a substituted resorcinol. By this method, cannabichromene is formed by heating olivetol and citral for several hours under reflux in the presence of pyridine, in molar proportions of 1:1:1 (olivetol:citrol:pyridine), with isolation of the product by direct chromatography on silica gel. The yields obtainable by this method, however, have only about 15 to 17% of theory. Methods have been proposed to increase the yield of varying the proportion of pyridine employed; however, molar proportions of 1:1:3 have only slightly increased cannabichromene yield to 20%, and molar proportions of 1:1:6 have significantly decreased the yield to about 5%. The acid-catalyzed condensation of olivetol and citral is also known, but the products of this reaction are not known to include cannabichromene.

The pyridine-catalyzed olivetol/citral condensation reaction also provides significant amounts of at least five by-products, in addition to unreacted material from which the cannabichromene must be separated. Both unreacted citral and the by-product isobichromene present difficulties during cannabichromene recovery, owing to the nearly identical $R_f$ values of cannabichromene and citral in different solvent systems and the very close $R_f$ values on silica gel of cannabichromene and isocannabichromene.

Accordingly, it is an object of this invention to provide a new method of synthesizing cannabichromene.

It is another object of this invention to provide an improved method for the recovery of cannabichromene.

It is an additional object of this invention to provide a composition useful for inducing hypothermia and useful as an antiinflammatory agent.

It is a further object of this invention to provide a new compound, 2-methyl-2(4-methyl-pent-3-enyl)-5-hydroxy-7-methylchromene, or CBC-$C_1$ as the compound will hereinafter be referred to.

It is an additional object of this invention to provide a method for reducing inflammation in mammals.

It is yet another object of this invention to provide a method for inducing hypothermia in mammals.

SUMMARY OF THE INVENTION

The invention comprises a method for preparing cannabichromene and homologues thereof in greatly improved yields by condensation of a substituted resorcinol and citral in the presence of a primary amine, and an improved method for separating the product from unreacted citral and isomeric by-products by first, reduction of citral to the corresponding alcohol and second, column chromatography on silica gel impregnated with 1% sodium hydroxide.

The invention further comprises a method for reducing inflammation and for inducing hypothermia in mammals comprising administering cannabichromene or its homologues to mammals either orally or by injection, in a therapeutically effective dose. Preferably, the compound is administered as a novel composition comprising a pharmaceutically-acceptable diluent carrier and cannabichromene or its homologues.

DETAILED DESCRIPTION OF THE INVENTION

According to the method for preparing cannabichromene or its homologues of the present invention (III), a substituted resorcinol (I) is condensed with citral (II) in the presence of a primary amine such as t-butylamine or n-propyl-amine according to the following reaction scheme:

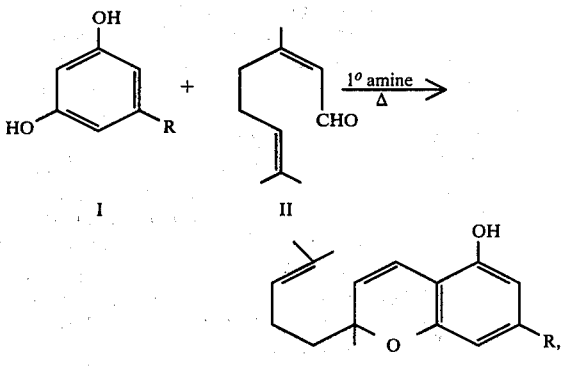

wherein R is hydrogen, $C_1$–$C_{10}$-alkyl, or $C_2$–$C_{10}$-alkenyl.

Of particular interest is the compound IV, CBC-C₁ formed from the condensation of orcinol (R is methyl) with citral:

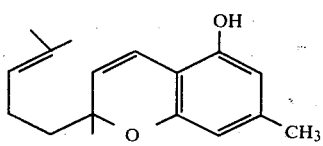

IV

In addition to the desired chromene products III, varying amounts of other by-products are formed in both the prior art and present condensation reactions, including an isomer of the chromene product (V), and a cannabicitran product (VI):

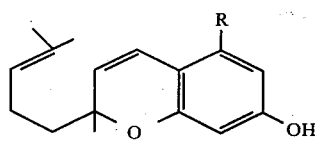

V

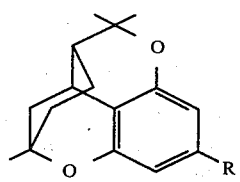

VI

The presence of these by-products substantially interferes with the purification of the chromene product III when conventional isolation procedures are employed. While the process of the present invention substantially decreases the formation of the by-products V and VI in contrast to prior art procedures, at least traces are usually present in the reaction product, and isolation of the chromene product III from the by-products V and VI is greatly facilitated by the improved separation method of the present invention.

Preferably, equimolar amounts of substituted resorcinol, citral, and primary amine are heated under reflux for about seven to nine hours, and the chromene product recovered from the crude reaction mixture by solvent extraction followed by chromatography of the extracted and partially purified product.

Preferably, toluene is employed as solvent in refluxing the reaction mixture, although other organic solvents such as methylene chloride are suitable, but may result in decreased yields. After reflux, the solvent is evaporated and the resultant crude reaction mixture is redissolved in an organic solvent such as benzene or cyclohexane, and this solution is then extracted with 1% aqueous sodium hydroxide and dried.

According to the process of the present invention, separation of CBC or its homologues (III) from unreacted citral (II) in this dried residue is accomplished by converting the citral to the corresponding alcohol which is much more polar than the chromene product. The citral is preferably reduced by sodium borohydride in alcohol such as ethanol, as this procedure does not significantly adversely affect the yield of the chromene III.

After reduction, the solvent is evaporated and the resultant crude dried residue partitioned between water and organic solvent and then chromatographed employing a solvent system of, for example, benzene-chloroform (1:1) or cyclohexane-chloroform (1:1). While conventional chromatographic procedures may be employed, chromatographic separation according to the present invention is preferred. By this method, the chromene product is purified by column chromatography on silica gel 60PF impregnated with 1% sodium hydroxide, which cleanly separates the chromene product (III) from the chromene isomer V. In the event that difficulties in separation of III from V are not contemplated, as, for example, when the isomer is present in only trace amounts, the crude product may be chromatographed by conventional methods such as on a column of processed silica gel, a column dry-packed with silica gel 60, or by high-pressure liquid chromatography. The yields of CBC by the process of the present invention are typically about 60% of theory.

Cannabichromene and its disclosed homologues has been found to be effective as antiinflammatory agents in mammals, and can be used to reduce inflammation and to relieve pain in diseases such as arthritis, as well as to reduce and control edema. Cannabichromene has also been found to be effective in inducing hypothermia which is useful, for example, when a decrease in metabolic activity is desired.

In both the rat-paw edema test and the eryrocytes membrane hemolytic test, CBC and CBC-C₁ were fond to be more effective than the standard phenylbutazone in controlling inflammation, as measured by reduced edema in rats and inhibition of heat-induced hemolysis of red blood cells.

Treatment for inflammation or to induce hypothermia is preferably by oral administration or intraperitoneal injection, in combination with a pharmaceutically-acceptable carrier which may be solid or liquid. Examples of acceptable solid carriers include, but are not limited to, starch, dextrose, sucrose, lactose, gelatin, agar, stearic acid, magnesium stearate, acacia, and similar carriers. Examples of liquids include, but are not limited to, water, edible oils, such as corn or peanut oils, and the like.

When administered in solid form, the compound and diluent carrier may be in the form of tablets, capsules, powders or lozenges prepared by standard techniques. When given as a liquid diluent carrier may be in the form of a liquid suspension administered as such or encapsulated.

When employed to treat an inflammatory condition in a mammal, animal, or human, the active compound is preferably administered orally in admixture with a pharmaceutically-acceptable diluent carrier as described above. When employed to induce hypothermia in a mammal, animal or human, the active compound is preferably administered by intraperitoneal injection, also an admixture with a pharmaceutically acceptable diluent carrier as described above. The compound is administered in a non-toxic dosage concentration sufficient to reduce the inflammation or edema where present, or to induce the desired degree of hypothermia. The actual dosage administered will be determined by such generally-recognized factors as the body-weight of the subject, the severity of the condition being treated, the idiosyncrasies of the particular subject, and the activity of the compound employed. With these considerations in mind, the dosage for a particular subject can be readily determined by the medical practitioner in accordance with conventional techniques in the medicinal art.

The following examples are illustrative of the invention.

EXAMPLES

EXAMPLE I (Preparation of Cannabichromene)

To a three-necked round bottomed flask (100 ml capacity), fitted with a dropping funnel and a condenser was added 5 g. olivetol (27.8 mmole) and 2.03 g. (2.96 ml., 27.8 mmole) t-butyl amine in 55 ml toluene and the mixture was heated to 50°–60° C., 4.23 g. (4.76 ml., 27.8 mmole) of citral was then added dropwise. The mixture was refluxed for 9 hours, after which time it was cooled to room temperature and the solvent evaporated to give 9.3 g. of crude reaction mixture. Gas chromatographic analysis of the reaction mixture showed 59.46% CBC (molar conversion), 5.04% cannabicitran and trace amount of iso-CBC.

EXAMPLE II (Purification of Cannabichromene)

5 g. of the crude reaction mixture from Example I was dissolved in 100 ml. benzene and the solution extracted twice with 50 ml. of 1% aqueous sodium hyroxide solution followed by 50 ml. of water. The benzene solution was then dried over anhydrous sodium sulfate and the solvent evaporated. The residue was then dissolved in 50 ml. ethanol, and 250 mg. of sodium borohydride were added portion-wise while stirring.

Stirring at room temperature was continued for 30 minutes after which time the solvent was evaporated and the residue partitioned between water (50 ml.) and benzene (100 ml.). The crude reaction mixture was chromatographed on a column of processed silica gel (200 g.). Processed silica gel was prepared by making a paste of silica gel -PF254 with water (equal amount) which was then dried in an oven at 110° and the resulting cake passed through 60 mesh sieve. The solvent system used was a mixture of benzene and chloroform (1:1). Fractions were collected and combined according to their tlc similarities in the same solvent system. Fractions containing pure CBC were combined, the solvent evaporated and the residue (2.1 g.) was analyzed by GC method and found to be 97% pure CBC. The synthetic CBC was found to be identical in all respects (tlc, GC, ir, uv, $^1H$ nmr and $^{13}C$-nmr) with authentic CBC [2-methyl-2-(4-methyl-pent-3-enyl)-5-hydroxy-7-pentyl chromene].

EXAMPLE III

The procedure of Example II was followed, except the crude reaction mixture was dissolved in cyclohexane instead of benzene. The same results were obtained.

EXAMPLE IV (Preparation of Cannabichromene)

To a three-necked, 2 liter round bottomed flask fitted with a condenser, a dropping funnel and a mechanical stirrer, was added 90 g. (0.5 mole) of powdered olivetol and 36.5 g. (53.2 ml., 0.5 mole) t-butylamine and the mixture dissolved in 1 liter toluene. The reaction mixture was then stirred for awhile when a brownish white gelatinous material appeared. The mixture was then heated to 50° C. and stirred constantly. To the resulting clear brown solution was added 76 g. (85.6 ml., 0.5 mole) citral dropwise. After complete addition of citral, the reaction mixture was refluxed for 9 hours, cooled to room temperature and the solvent evaporated to give 166.8 g. of crude reaction mixture.

Dry weight analysis of the crude mixture using gas liquid chromatography showed 62.05% CBC, 5.09% Cannabicitran and trace amount of iso-CBC. Cannabichromene was purified and chromatographed in the same manner as previously described under Example II.

EXAMPLE V (Preparation of Cannabichromene)

The reaction of 5 g. olivetol (27.8 mmole), 1.652 g. n-propylamine (2.3 ml., 27.8 mmole) and 4.6 ml. citral (27.8 mmole) in 55 ml. toluene was carried out in the same manner as described under Example 1. The refluxing time was 7 hours. Gas chromatographic analysis of the reaction mixture showed 61.62% CBC, 4.01% Cannabicitran and trace amount of iso-CBC.

Purification and chromatography of CBC were carried out as described under Example II.

EXAMPLE VI (Preparation of the Methyl Homologues of Cannabichromene)

Th procedure described in Example I was followed, except 3.45 g of orcinol was reacted in place of the 5 g. of olivetol. Gas chromatographic analysis of the reaction mixture showed 48.27% yield of $CBC-C_1$.

EXAMPLE VII (Purification of $CBC-C_1$)

The product of Example VI was purified according to the process of Example II. The product was found to be pure $CBC-C_1$ as a pale yellowish oil, the identity of which was determined as 2-methyl-2(4-methyl-pent-3-enyl)-5-hydroxy-7-methylchromene by comparison of the spectral data with those of CBC.

EXAMPLE VIII

[Inhibition of Inflammation of CBC, as Measured by the Rat-Paw Edema Test (Intraperitoneal Injection)]

A. Procedure

The test rats were divided into test groups of 6 to 8 animals, weighed and marked so that the individual rats could be identified; all rats were given a 700 mg/kg intraperitoneal injection of ethyl urethane in distilled water to render them tractable during testing. A circle was drawn, with a felt-tipped mixer, around the hind leg of each rat just above the ankle, and each rat was dosed with a test or control compound by intraperitoneal injection. Test compounds were given at doses of 60, 120, 240, or 480 mg/kg. The negative control was the vehicle which was used to give the test compounds and the two positive controls were phenylbutazone given at 120 mg/kg and 60 mg/kg. Phenylbutazone was prepared for injection by suspending it in normal saline using Tween 60. The rats were then held in group cages for 30 minutes. The volume of the left hind paw was measured using a mercury displacement pleysmograph.

The paw was dipped into the mercury until the mercury touche the line above the ankle. Mercury was then withdrawn until the mercury returned to its original level. The amount of mercury removed was measured in milliliters (ml). The mercury can be measured accurately to 0.01 ml. The left hind paw was then injected with 0.1 ml of a 5% w/v solution of viscous carageenen in normal saline. The injection was given between the metatarsal bones using a 27 gauge needle, and the rats then held in group cages for 3 hours. The volume of the left hind paws was measured again in the pleysmograph. The results were computed in the following manner:

a. A mean is taken for both the preinjection and post-injection paw volume of each test group.
b. The mean difference in volume (MDV) for each test group is computed by subtracting the preinjection mean from the postinjection mean.
c. The percent of control is computed for each test group as:

$$\% \text{ of control} = \frac{MDV \text{ control group}}{MDV \text{ test group}} \times 100$$

The percent of control is used to compare the efficacy of the various drug treatments.

d. The percent increase in paw volume is calculated for each group as:

$$\% \text{ increase} = \left( \frac{\text{Postinjection Mean}}{\text{Preinjection Mean}} \times 100 \right) - 100$$

The percent increase is used to compare the amount of edma observed in one experiment to the amount of edma observed in other experiments.

B. Results

The data from the rat paw test were further analyzed using a one-way analysis of varience (ANOVA) and Duncan's New Multiple Range Test. The results of these tests are given in Tables 2 and 3. The pre-injection score of each animal was subtracted from his post-injection score and an analysis of the different scores was conducted. The analysis showed that all test groups differed significantly from the vehicle control group. The 120 mg/kg dose of CBC differed significantly from the 240 and 480 mg/kg doses of CBC, and the 480 mg/kg dose of CBC differed significantly from the 120 mg/kg dosage of PBZ.

No significant effects were seen on the CNS screen at doses of CBC as large as 800 mg/kg in unanethetized mice.

TABLE 1

RAT - PAW EDEMA DATA

| COMPOUND | DOSE | MDV | PERCENT OF CONTROL | PERCENT INCREASE |
| --- | --- | --- | --- | --- |
| Vehicle Control | 0.5 ml | 0.463 | 100.000 | 42.383 |
| CBC | 120 MG/KG | 0.139 | 30.000 | 12.729 |
| CBC | 240 MG/KG | 0.004 | 0.927 | 0.365 |
| CBC | 480 MG/KG | −0.043 | −9.189 | −3.708 |
| PBZ | 120 MG/KG | 0.106 | 22.973 | 10.316 |

Percent of Control and Percent Increase Computed before Rounding MDVS or Group Means.

TABLE 2

Analysis of varience for difference scores from rat-paw edema test.

| Source | $\Sigma x^2$ | df | MS | F |
| --- | --- | --- | --- | --- |
| Among | 1.2291 | 4 | 0.3073 | 24.434** |
| Within | 0.4311 | 34 | 0.0128 | |
| Total | 1.6602 | 38 | | |

**$p. < 0.01$

TABLE 3

Duncan's Test for Difference Scores Rat-Paw Edema Test.

| Group | $\bar{x}$ | $I_0$ | $I_1$ | $I_2$ | $I_3$ | SSR+ |
| --- | --- | --- | --- | --- | --- | --- |
| Vehicle control | 0.463 | — | .0324** | 0.356** | 0.458** | 0.505** | 0.170 / 0.128 |
| CBC 120mg/kg | 0.139 | — | — | 0.033 | 0.134* | 0.181** | 0.167 / 0.125 |
| PBZ 120mg/kg | 0.016 | — | — | — | 0.102 | 0.149* | 0.162 / 0.121 |
| CBC 240mg/kg | 0.004 | — | — | — | — | 0.047 | 0.156 / 0.115 |
| CBC 480mg/kg | 0.043 | — | — | — | — | — | |
| | | Vehicle control | CBC 120mg/kg | PBZ 120mg/kg | CBC 240mg/kg | CBC 480mg/kg | |

*$p. < 0.05$
**$p. < 0.01$
+Shortest significant range for the 0.05 and 0.01 levels of significance.

The results of the rat-paw edema test are summarized in Table 1. As can be seen, doses of 120, 240, and 480 mg/kg all produced strong antiinflammatory effects. The effects were shown to be dose related, that is, higher doses of CBC produced stronger antiinflammatory effects. All the animals receiving 480 mg/kg died within 2 days of injection, but this cannot be judged to be simply a result of CBC toxicity since the rats also received an IP injection of 750 mg/kg of ethyl urethane as part of the test procedure. Seven of the eight animals receiving 240 mg/kg of PBZ died before the test could be completed. The eighth rat died within 24 hours of injection.

EXAMPLE IX

[Inhibition of Inflammation of CBC as Measured by the Rat-Paw Edema Test (oral administration]

A. Procedure: The procedure described in Example VIII was followed, except the rats were dosed by oral gauge instead of i.p. injection. The test was conducted twice, once with nonfasted rats and once with rats that had been fasted during the 24 hour period prior to dosing. The 60 mg/kg Penylbutazone control group was not used in the test with fasted animals. Tween 60 in normal saline was the vehicle control for the non-fasted rats and normal saline was the vehicle control for the fasted rats.

B. Results: The results are given in Tables 4 and 5. As can be seen from the tables, cannabichromene was active at all the doses tested. The degree of inhibition of edema increased in both tests as the amount of CBC given was increased. The degree of inhibition was greater in the fasted rats than it was in the nonfasted rats. This would be expected since the fasted rats should absorb the test compound more readily than the nonfasted rats.

When CBC is compared to PBZ in Tables 1 and 2 it is seen that PBZ was slightly more effective than CBC at 120 mg/kg in the nonfasted rats and that CBC and PBZ were about equally effective at 120 mg/kg in the fasted rats. The higher doses of CBC were generally more effective in inhibiting edema than was PBZ. PBZ was not given at higher doses because of the rapid deaths produced by 240 mg/kg of PBZ given intraperitoneally in the test described in Example VIII.

TABLE 4
RAT - PAW EDEMA DATA
Oral CBC in Non-Fasted Rats. Run 11-6-1978

| COMPOUND | DOSE | MDV | PERCENT OF CONTROL | PERCENT INCREASE |
|---|---|---|---|---|
| Vehicle Control | 0.5 ml | 0.625 | 100.000 | 58.140 |
| CBC | 120 MG/KG | 0.496 | 79.400 | 41.311 |
| CBC | 240 MG/KG | 0.412 | 66.000 | 38.372 |
| CBC | 480 MG/KG | 0.315 | 50.400 | 29.200 |
| PBZ | 60 MG/KG | 0.489 | 78.200 | 50.257 |
| PBZ | 120 MG/KG | 0.392 | 62.667 | 36.098 |

Percent of Control and Percent Increase Computed Before Rounding MDVS or Group Means.

TABLE 5
RAT - PAW EDEMA DATA
Oral CBC in Fasted Rats. Run 11-14-1978

| COMPOUND | DOSE | MDV | PERCENT OF CONTROL | PERCENT INCREASE |
|---|---|---|---|---|
| Saline Vehicle Control | 0.5 ml | 0.625 | 100.000 | 46.339 |
| CBC | 120 MG/KG | 0.409 | 65.400 | 31.382 |
| CBC | 240 MG/KG | 0.209 | 33.400 | 15.981 |
| CBC (given following saline infusion) | 480 MG/KG | 0.281 | 45.000 | 22.321 |
| PBZ | 120 MG/KG | 0.403 | 64.400 | 31.051 |

Percent of Control and Percent Increase Computed Before MDVS or Group Means.
*Doses are Approximate Due to an Error in Procedure.

EXAMPLE X

[Inhibition of Inflammation by CBC as Measured by Inhibition of Erythema (Red-Blood Cell Hemolysis)]

A. Procedure: The red blood cells (RBC's) were sensitized by washing twice with a volume of saline equal to the initial blood volume. CBC was suspended in a 2% ethanol in saline solution because of its insolubility in water. The procedure was duplicated successfully 3 times using either 40% or 20% RBC suspensions.

B. Results: CBC was screened for inhibition of red cell hemolysis. The results of the tests are shown in Table 6. Phenylbutazone (PBZ), aspirin and tolmetin were used as positive controls and all inhibited heat induced hemolysis at the concentration tested. Inhibition of hemolysis was dose-related in the positive controls and cannabichromene groups (Test 3). CBC produced 35% inhibition of heat-induced red cell hemolysis at $10^{-4}$ M test concentration and 26% at $2 \times 10^{-5}$ M CBC. PBZ produced 16% and 10% inhibition of red cell hemolysis at the $10^{-4}$ M and $2 \times 10^{-5}$ M test levels, respectively. Aspirin produced a 40% inhibition at the $5 \times 10^{-4}$ M Test concentration.

It was apparent that not all the CBC actually went into suspension. In order to determine if some of the CBC adhered to the wall of the glassware a 10 ml aliquot of the $2 \times 10^{-4}$ (solution a) of CBC saturated with Nacl was extracted with $CHcl_3$ and analyzed by G.C. The solution was found to be $2 \times 10^{-5}$ M CBC or to contain 0.3 mg of the original CBC. The flask was rinsed with ethanol and the washings analyzed by GC and found to contain 1.355 mg of CBC. The remaining 1.475 mg (50%) of CBC that could not be accounted for by G.C. analysis may have been lost during the extraction procedure or while adjusting the pH of the test solution. If the 1.475 mg CBC which could not be accounted for was actually in suspension then the maximum final concentration of CBC used in the highest CBC test level would be $5 \times 10^{-5}$ M or one half the amount listed in Table 6. In summary, CBC, at a minimum, produces 2 to 2½ times more inhibition of heat induced red cell hemolysis than does PBZ at equimolar concentrations. Inhibition of heat-induced hemolysis was seen over a range of $10^{-4}$ M to $2 \times 10^{-6}$ M CBC. The actual activity of CBC may have been 3 to 30 times more protective of red cell membranes than an equivalent amount of PBZ.

TABLE 6

| (Inhibition of Heat-Induced Erythrocyte Hemolysis) | | | |
|---|---|---|---|
| Final Concentration of | Percent Inhibition | | |
| the TEST SOLUTION | TEST 1* | TEST 2 | TEST 3 |
| Phenylbutazone | | | |
| $2.5 \times 10^{-4}$M | 54 | 70 | 49 |
| $1.0 \times 10^{-4}$M | | | 16 |
| $2.5 \times 10^{-5}$M | 31 | | |
| $2.0 \times 10^{-5}$M | | | 10 |
| Acetylsalicylic Acid | | | |
| $5.0 \times 10^{-4}$M | | | 40 |
| $2.5 \times 10^{-4}$M | 21 | | |
| Tolmetin | | | |
| $2.0 \times 10^{-4}$M | 27 | | |
| Cannabichromene | | | |
| $1.0 \times 10^{-4}$M | | 40 | 37 |
| $1.0 \times 10^{-4}$M | | | 33 |
| $2.0 \times 10^{-5}$M | | 26 | 26 |
| $2.0 \times 10^{-6}$M | | | 7 |

*A 20% RBC suspension was used for Tests 1 and 3.
A 40% RBC solution was used for Test 2.

EXAMPLE XI (Inducement of Hypothermia by CBC in Mice)

A. Procedure: CBC (100 mg/kg was prepared in emulsion form with 3% Tween 60 and 3% Arlacel in normal saline (0.9%) in such a way as to permit a volume of 10 ml/kg of body weight to be injected intraperitoneally into male mice weighing between 32 and 38 grams.

The animals were divided into groups of 10, and body temperatures were recorded with a multichannel Yellow Springs Telethermometer and Thermistor probes. During the experiment, the mice were confined in plastic restraint tubes. They were allowed 45-60 min. for adaption to the restraint tubes and to rectal thermistor before a pre-drug baseline temperature reading was taken. Body temperature readings were obtained at 0.5, 1.0, 2.0, 3.0 and 4.0 hrs. post-CBC administration.

The mean (±S.E.) decrease in temperature from the preinjection baseline reading for saline-, vehicle-, and CBC-treated mice were calculated and statistical analyses were conducted using the two-tailed Student's t test.

B. Results: As summarized in Table 7, both the CBC- and vehicle control-treated groups showed a consistent drop in body temperature over the duration of the experiment, with the CBC-induced hypothermia being more pronounced and significantly different from saline controls at all readings, whereas the vehicle induced decrease in body temperature was only significant from saline controls at the 2.0, 3.0 and 4.0 hr. readings.

TABLE 7

| | Mean (±S.E.) Decrease in Rectal Temp. (°0) Time (hrs.) | | | | |
|---|---|---|---|---|---|
| Treatment | 0.5 | 1.0 | 2.0 | 3.0 | 4.0 |
| Normal Saline | 0.43 ± 0.12 | 0.44 ± 0.07 | 0.47 ± 0.07 | 0.61 ± 0.14 | 0.60 ± 0 |
| Vehicle Control | 0.58 ± 0.16 | 0.80 ± 0.16 | 1.62 ± 0.16* | 1.35 ± 0.14* | 1.04 ± 0* |
| CBC (100 mg/kg) | 1.86 ± 0.18$^\Delta$* | 2.52 ± 0.26$^\Delta$* | 1.93 ± 0.21* | 1.53 ± 0.21* | 1.61 ± 0*$^\Delta$ |

*Significantly different from saline controls, $P \leq 0.05$.
$\Delta$Significantly different from vehicle control, $P \leq 0.05$.

In spite of the vehicle's activity, the hypothermia induced by CBC was still significantly different from vehicle controls at 0.5, 1.0 and 4.0 hrs.

The peak hypothermic effect (at a dose of 100 mg/kg, i.p.) for CBC was attained within the first two hours and then declined thereafter.

EXAMPLE X

[Inhibition of Inflammation by CBC-$C_1$ as Measured by the Rat-Paw Edema Test (intraperitoneal administration)]

A. Procedure: The procedure described in Example VIII was followed. CBC-$C_1$ was tested at doses of 60 mg/kg and 120 mg/kg prepared in an emulsion with Tween 60, Arlacel and distilled water. The vehicle control used was Tween 60, Arlacel and distilled water prepared without CBC-$C_1$.

B. Results: The results are given in Table 8. CBC-$C_1$ was active at both 60 mg/kg and 120 mg/kg. The inhibition of edema was dose related. When the effects of CBC-$C_1$ were compared with those of PBZ it can be seen that CBC-$C_1$ did reduce the rat paw edema with slightly less activity than PBZ at the 120 mg/kg dose and was as active as PBZ at 60 mg/kg. No toxic or adverse effects were observed in any of the rats tested.

TABLE 8

| | RAT - PAW EDEMA DATA CBC-$C_1$ given i.p. in fasted rats. Run 5-10-79 | | | |
|---|---|---|---|---|
| COM-POUND | DOSE | MDV | PERCENT OF CONTROL | PERCENT INCREASE |
| Vehicle Control | 0.00 MG/KG | 0.191 | 100.000 | 13.947 |
| CBC-$C_1$ | 120 MG/KG | 0.070 | 36.601 | 4.956 |
| CBC-$C_1$ | 60 MG/KG | 0.090 | 47.059 | 6.742 |
| PBZ | 120 MG/KG | 0.046 | 24.183 | 3.254 |
| PBZ | 60 MG/KG | 0.090 | 47.059 | 6.742 |

Percent of Control and Percent Increase Computed Before Rounding MDVS or Group Means.

Although this invention has been described with reference to illustrative embodiments thereof, it will be apparent to those skilled in the art that the principles of this invention can be embodied in other forms within the scope of the following claims.

What is claimed is:

1. A method for the preparation of cannabichromene and cannabichromene analogues of the formula

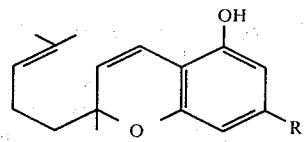

wherein R is hydrogen, $C_1$–$C_{10}$-alkyl or $C_2$–$C_{10}$-alkenyl, comprising reacting a substituted resorcinol of the formula

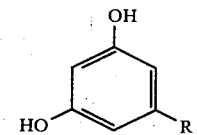

wherein R is hydrogen, $C_1$–$C_{10}$-alkyl or $C_2$–$C_{10}$-alkenyl with citral in the presence of a primary amine.

2. The method of claim 1 for the preparation of cannabichromene comprising the steps of condensing olivetol and citral in the presence of a primary amine and separating the cannabichromene from the reaction mixture.

3. The method of claim 1, wherein the primary amine is t-butylamine.

4. The method of claim 1, wherein the primary amine is n-propylamine.

5. The method for preparing cannabichromene of claim 2 comprising treating the condensation reaction product with a reducing agent followed by chromatographing the so treated reaction mixture on silica gel impregnated with 1% sodium hydroxide solution to obtain substantially pure cannabichromene.

6. The method of claim 5, wherein the reducing agent is sodium borohydride in ethanol.

7. A method for preparing cannabichromene in high yields comprising (a) condensing olivetol and citral in the presence of a primary amine under reflux in an organic reflux solvent to provide a crude reaction product, (b) evaporating the reflux solvent and dissolving the resultant dried crude reaction mixture in an extraction solvent, (c) extracting the dissolved reaction mixture followed by evaporation of the extraction solvent to form a dried crude residue, (d) dissolving the residue in ethanol and adding sodium borohydride to reduce unreacted citral to the corresponding alcohol, (e) evaporating the ethanol and chromatographing the residue employing a chromatography solvent system on a column of silica gel impregnated with 1% sodium hydroxide, and (f) recovering substantially purified cannabichromene.

8. The method of claim 7 wherein the reflux solvent is toluene.

9. The method of claim 7 wherein the extraction solvent is benzene or cyclohexane.

10. The method of claim 7, wherein the chromatography solvent system is benzene-chloroform (1:1) or cyclohexane-chloroform (1:1).

* * * * *